US00PP31435P2

(12) United States Plant Patent
Hansen

(10) Patent No.: US PP31,435 P2
(45) Date of Patent: Feb. 4, 2020

(54) ***SALVIA* PLANT NAMED 'PINK PROFUSION'**

(50) Latin Name: *Salvia nemorosa*
Varietal Denomination: Pink Profusion

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,489

(22) Filed: Nov. 21, 2018

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/00; A01H 5/02; A01H 6/508
See application file for complete search history.

*Primary Examiner* — Keith O. Robinson

(57) ABSTRACT

A new and distinct cultivar of perennial *Salvia* plant named 'Prefect Profusion' characterized by its dark pink flowers in densely arranged in verticils with dark wine-colored calyces and matching bracts. The new plant has a compact habit with stiff, upright, heavily-branched stems with strong tendency to repeat when deadheaded, a strong vigorous growth rate and rugose gray-green foliage. It is useful for landscaping specimens, en masse or as a container plant.

1 Drawing Sheet

Botanical denomination: *Salvia nemorosa.*
Cultivar designation: 'Pink Profusion'.

STATEMENT REGARDING PRIOR DISCLOSURES UNDER 37 CFR 1.77(b)(6)

The first public disclosure of the claimed plant, in the form of a sale, was made by Walters Gardens, Inc. on Apr. 10, 2018. Prior to that, on Dec. 1, 2017 the claimed plant was displayed with a photograph and brief description in a website operated by Walters Gardens, Inc., who obtained the plant and all information relating thereto, from the inventor. No plants of *Salvia* 'Pink Profusion' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'Pink Profusion' or as the new plant. The new plant was selected from an insect-pollinated cross between the female parent, an unreleased proprietary hybrid known only by the breeder code 12-98-1 (not patented) and an unnamed sibling of 12-98-1 (not patented) in May of 2013 at an isolation block at a wholesale perennial nursery in Zeeland, Mich. Seeds were collected in June of 2013 and the new plant begun the trial phase in the summer of 2015 and eventually assigned the breeder code 13-64-130 prior to assigning a cultivar name.

The new *Salvia* was further evaluated and asexually propagated first by division in 2015 and propagated by basal cuttings taken at the same nursery in Zeeland, Mich., USA in June of 2016. Evaluation of these and further cutting grown plants shows that *Salvia* 'Pink Profusion' continues to be stable and produce true to type plants in successive generations of asexual propagation.

SUMMARY OF THE INVENTION

Plants of *Salvia* 'Pink Profusion' can be most closely compared to *Salvia* 'Bumbleberry' U.S. Plant patent application Ser. No. 15/731,913, 'Sensation Rose' U.S. Plant Pat. No. 18,230 and 'Rose Queen' (not patented). 'Sensation Rose' and 'Rose Queen' have shorter habit. 'Rose Queen' has larger magenta purple flowers with less repeating flowering. 'Bumbleberry' is shorter in habit and produces less repeat flowering when deadheaded.

The following characteristics in combination distinguish *Saliva* 'Pink Profusion' as a new and distinct cultivar from all other cultivars known to the inventor:

1. Dark pink flowers densely arranged in dense verticils;
2. Stiff, upright, heavily-branched flower stems;
3. Strong repeat flowering when deadheaded;
4. Compact, rounded, strong, vigorous and winter-hardy habit;
5. Rugose gray-green foliage.

BRIEF DESCRIPTION OF THE DRAWINGS

The photographs of the new plant demonstrate the unique traits and the overall appearance of *Salvia* 'Pink Profusion'. The colors are as accurate as reasonably possible with color reproductions. Variation in ambient light spectrum, source and direction may cause the appearance of minor variation in color. The plant used in the photographs was a three-year-old plant grown in an open, full-sun trial garden at a wholesale perennial nursery in Zeeland, Mich. with supplemental water and fertilizer when needed. Plant growth regulators have been used in greenhouse grown trials only.

DETAILED BOTANICAL DESCRIPTION

Figure 1:
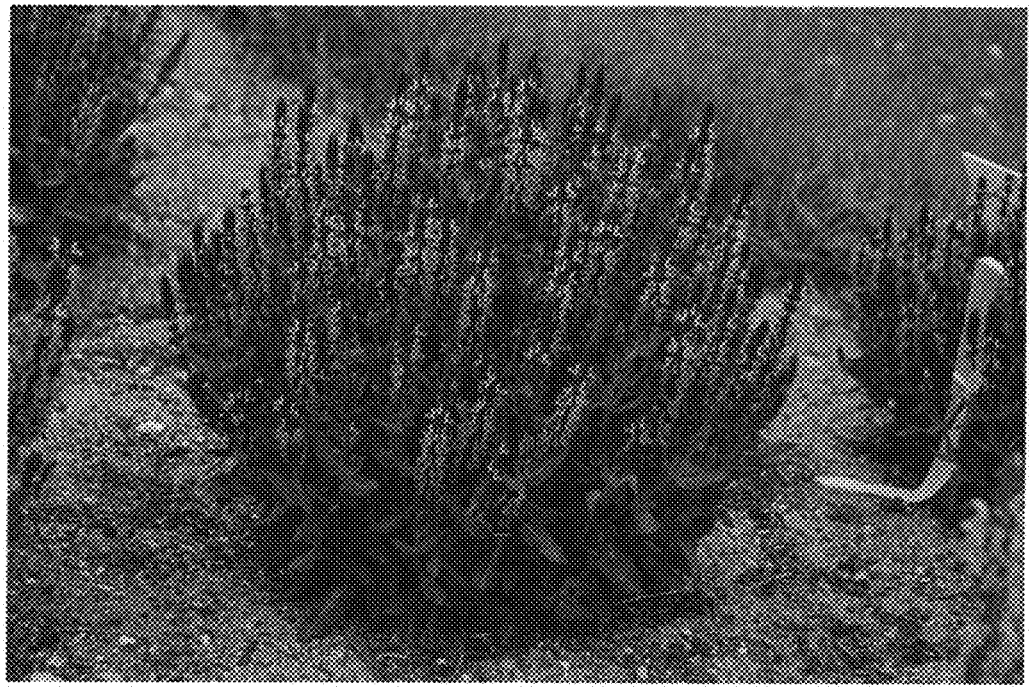
FIG. 1 shows the plant habit in full flower in a landscape.
Figure 2:
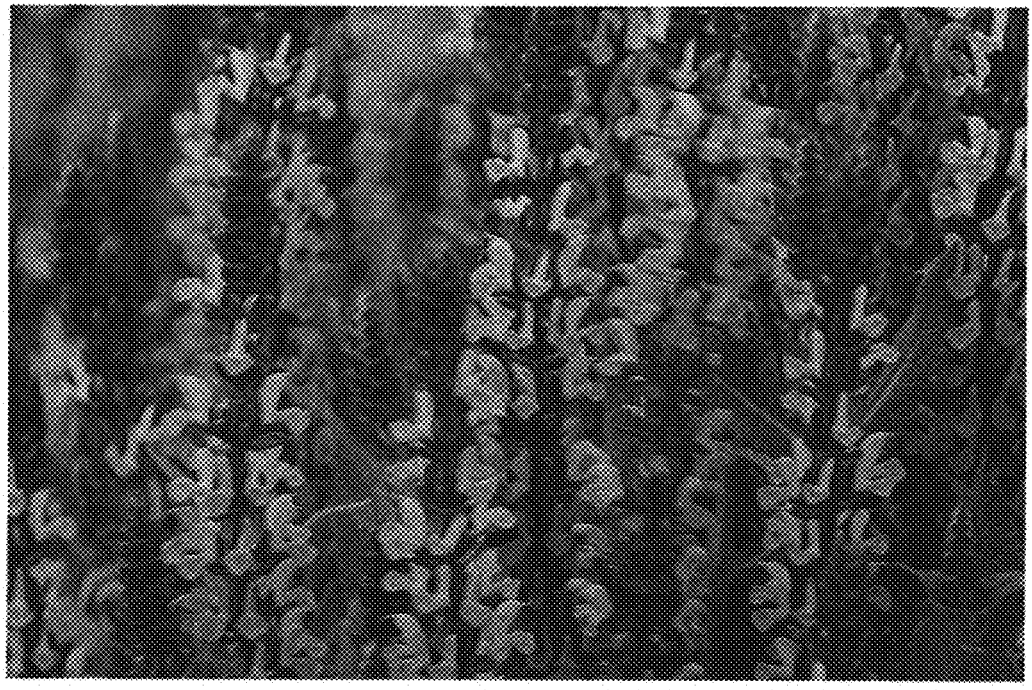
FIG. 2 shows a close-up of the flower scapes with the buds, flowers, stems and calyxes.

The following descriptions and color references except where common dictionary terms are used are based on The 2015 edition of The Royal Horticultural Society Colour Chart. *Salvia* 'Pink Profusion' has not been observed under all possible environments. The phenotype may vary slightly with different growing environments such as temperature, light, fertility, soil pH, moisture and plant maturity levels, but without any change in the genotype. The following observations and size descriptions are based on three-year-old plants growing in an outdoor full-sun trial garden and in a greenhouse at a wholesale perennial nursery in Zeeland, Mich. and greenhouse forced two-year-old plants. Plants were given supplemental water and fertilizer.

Botanical classification: *Salvia nemorosa* (Linnaeus);

Parentage: Female or seed parent the unreleased hybrid 12-98-1; the male or pollen parent is a sibling to hybrid 12-98-1;

Plant habit: Winter-hardy herbaceous perennial; multi-stemmed, compact, rounded, with basal and cauline foliage, and flowers in several, tightly-arranged verticils on highly-branched upright racemes displayed above foliage; flowering to about 41.0 cm tall and about 52.0 cm wide at the fullest point about 20 cm above soil; with cauline foliage below branches;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks;

Root description: Fine, well-branched; color dependent on age and soil type, from cream to dark tan in color; typically nearest RHS 161D;

Foliage: Opposite, simple, rugose, lanceolate; margin bi-crenulate; glabrous and matte abaxial and adaxial surfaces; acute apex and base cordate to truncate; leaf blades about 9.5 cm long and 4.0 cm across, decreasing in size distally; average about 7.2 cm long and 2.5 cm across; faint sage fragrance; leaf variegation absent;

Foliage color: Adaxial surface between RHS NN137C and RHS 137A; abaxial surface nearest RHS 147B;

Venation: Reticulate; impressed on adaxial side and costate on. abaxial side; abaxial midrib puberulent secondary veins glabrous; adaxial puberulent;

Vein color: Adaxial midrib between RHS 146D and RHS 145D, secondary veins nearest RHS 148D; abaxial midrib nearest RHS 145D and primary and secondary veins nearest RHS 148D;

Petiole: Concavo-convex; puberulent adaxial and abaxial and ciliolate margin distally and ciliate proximally; to about 5.5 cm long and 6.0 mm wide, average 4.0 cm long and 4.5 mm wide at base;

Petiole color: Adaxial and abaxial surfaces nearest 145B in center with margin nearest RHS 138A;

Inflorescence description: Perfect, bilabiate, verticillate with flowering generally beginning at lower verticils and advancing up the scape, but not all flowers at each verticil opening at the same time giving the effect of a scape being in continuous flower for longer periods; average distance between verticils about 1.5 mm, greater proximally and less distally; self-cleaning, petals not persistent; flowering beginning late spring for about six weeks and repeating if initial scapes removed; total length about 45 cm long, flowering in upper 15 cm and branching to about 7 cm wide; average internode distance about 6 mm; number of flowers per node or verticil about 12 in lowest nodes, decreasing distally;

Inflorescence attitude: With midline projected about 30 degree angle above horizontal and hood petal about 55 degree angle above horizontal;

Flower longevity: About four days on the plant or as cut flower;

Fragrance: None detected under present growing conditions;

Flower buds one day prior to anthesis: Shape is rounded on top and slightly concave below, with rounded apex; micro-puberulent; about 9.0 mm long, 3.0 mm tall and 2.0 mm wide;

Bud color: Exposed dorsal petal nearest RHS 70C, ventral petal nearest RHS N78C; abaxial calyx nearest RHS 138A with veins and dorsal portion nearest RHS 187B;

Flowers: Bilabiate corolla with arcuate hooded upper lip and tri-lobed lower lip; about 12.0 mm long, 7.5 mm tall and 5.0 mm wide fused into tube in the proximal 5.0 mm; clustered at verticils with up to 8 flowers per verticil;

Petals: Bilabiate corolla; upper hood petal and flattened side to side vertically, with emarginate apex and base fused with labium;

Hood (upper) petal: Minutely puberulent outside, glabrous inside; about 9.0 mm long, 3.0 mm tall and 2.0 mm across;

Labium (lower) petal: Consisting of three lobes, two proximal lobes projecting outwardly, about 2.0 mm long and 1.0 mm wide at base with rounded apex; center lobe rounded emarginate apex, about 5.0 mm long 5.5 mm wide with a 2.0 mm apical notch at apex; center lobe slightly concaved upwards; total labium about 8.0 mm long, 5.5 mm wide at the widest portion across middle of central lobe and 4.5 mm tall;

Petal color: Abaxial hood nearest RHS 77B and adaxial hood petal nearest RHS 75D; lower labium petal proximal lobes abaxial between RHS 77A and RHS 77B, and adaxial nearest RHS 77A and center lobe abaxial between RHS 77A and RHS 77B, and adaxial nearest RHS 77A;

Androecium: Two, fused with labium, contained within hood petal except when triggered by pollinator;

*Filament.*—Glabrous, fused about 4.0 mm from base of labium petal; curved around inside of hood petal; about 2.5 mm long and less than 0.3 mm diameter with a 1.0 mm trip mechanism at base; color nearest RHS NN155D.

*Anther.*—Glabrous, oblong, about 1.0 mm long and 1.0 mm diameter; longitudinal, basifixed; color nearest RHS 162D.

*Pollen.*—Not found.

Gynoecium: One, superior; curved around inside of hood petal;

*Style.*—About 10.5 mm long and about 0.3 mm diameter; color nearest RHS NN155D in basal 5.0 mm and gradually darkening distally to nearest RHS 77A before stigma split.

*Stigma.*—Bifurcate and curved in the terminal 2.0 mm; apex acute; color between RHS N79B and RHS 79B.

*Ovary.*—Superior; color nearest RHS N144A.

Fruit: Nutlet, one to four per flower; rounded, about 1.5 mm diameter; color nearest RHS 202A;

Calyx: Campanulate; consisting of five sepals, three upper and two lower; 7.0 mm long and 2.5 mm across at apex;

Sepals: Five; fused in basal 3.5 mm; lower set split bifid in distal 2.5 mm, upper set trifid in distal 0.5 mm; tube about 6.5 mm long and 5.0 mm tall at mouth and 3.0 mm wide; lower set bifurcate in terminal 2.5 mm; upper set of trifurcate in distal 1.0 mm; glandular abaxial and glabrous adaxial;

Sepal color: In low light abaxial base nearest RHS 144A with veins and distal blushing of nearest RHS N186D, abaxial in high light nearest RHS N186C; adaxial base between RHS 194D and RHS 145D with veins nearest RHS 146B and distal tinting nearest N186C;

Bracts: Each verticil subtended by two opposite ovate to nearly cordate bracts; apex typically acuminate; base truncate; margin crenate and ciliolate; coarsely wavy to bent downward toward apex; glabrous above and pubescent below; bract size up to 11.0 mm long and 8.0 mm wide, decreasing distally;

Bract color: In high light between RHS N186C and RHS 187C on both adaxial and abaxial;

Peduncles: Raceme; pubescent; quadrangular in cross section; about 14 per plant; strong; upright; to about 42.0 cm tall and 4.0 mm across at base; flowering in upper 20.0 cm and to about 27.0 cm across with branches; compound branches in lower two to four nodes, upright at 50 to 60 degrees above horizontal; branches to about 18.0 cm long and 3.0 mm across; average internode distance about 4.5 cm;

Peduncle color: Nearest RHS 146C;

Pedicels: Cylindrical; puberulent to glandular; about 0.5 mm long and 0.5 mm diameter; slightly upright to nearly horizontal at flower anthesis and with seed set;

Pedicel color: Nearest RHS 187A;

Disease and pest resistance: Resistant to diseases and pests beyond that common to *Salvia* has not been noted. Specific diseases have not been tested, but not commonly browsed by *Cervinea* or *Oryctolagus*.

Growth recommendations: Plants of *Salvia* 'Pink Profusion' perform best with adequate moisture and good drainage and are hardy from USDA zone 3 to 8.

It is claimed:

1. A new and distinct perennial *Salvia* plant named 'Pink Profusion' as herein described and illustrated.

* * * * *